(12) United States Patent
Albanese et al.

(10) Patent No.: US 10,130,541 B2
(45) Date of Patent: Nov. 20, 2018

(54) DEVICE FOR SUPPORTING A PATIENT TO ALLOW PERFORMANCE OF A BREAST EXAM

(71) Applicant: I.M.S. INTERNAZIONALE MEDICO SCIENTIFICA S.r.l., Sasso Marconi (Bologna) (IT)

(72) Inventors: Achille Albanese, Marzabotto (IT); Bruno Toniolo, Sasso Marconi (IT); Paolo Vignoli, San Giovanni in Persiceto (IT); Sara Vecchio, Casalecchio di Reno (IT)

(73) Assignee: IMS GIOTTO S.P.A., Sasso Marconi (BO) (IT)

( * ) Notice: Subject to any disclaimer, the term of this patent is extended or adjusted under 35 U.S.C. 154(b) by 212 days.

(21) Appl. No.: 14/868,649

(22) Filed: Sep. 29, 2015

(65) Prior Publication Data
US 2016/0089292 A1 Mar. 31, 2016

(30) Foreign Application Priority Data
Sep. 30, 2014 (IT) .......................... BO2014U0080 U (51) Int. Cl.
*A61G 13/06* (2006.01)
*A61G 13/08* (2006.01)
*A61G 13/00* (2006.01)
*A61B 6/04* (2006.01)

(52) U.S. Cl.
CPC ......... *A61G 13/06* (2013.01); *A61G 13/0018* (2013.01); *A61G 13/08* (2013.01); *A61B 6/0435* (2013.01); *A61G 2200/12* (2013.01); *A61G 2200/325* (2013.01)

(58) Field of Classification Search
CPC .... A61G 13/06; A61G 13/08; A61G 13/0018; A61G 13/12; A61G 13/121; A61G 13/122; A61G 13/125; A61G 2200/12; A61G 2200/325; A47C 20/025; A61B 6/0435; A61B 5/708; A61B 5/0091
See application file for complete search history.

(56) References Cited

U.S. PATENT DOCUMENTS

| | | | | | |
|---|---|---|---|---|---|
| 3,921,230 | A | * | 11/1975 | Hanning | A47C 20/041 5/616 |
| 4,195,829 | A | * | 4/1980 | Reser | A61G 13/02 5/607 |
| 5,415,169 | A | * | 5/1995 | Siczek | A61B 6/0435 348/E13.014 |

(Continued)

*Primary Examiner* — Nicholas F Polito
(74) *Attorney, Agent, or Firm* — Shuttleworth & Ingersoll, PLC; Tiimothy J. Klima (57) ABSTRACT

A device for supporting a patient to allow an exam to be performed on the patient's breast, including a supporting table which has a longitudinal axis of extension and on which the patient can lie in a reclining position; the supporting table is provided, in proximity to one end of it, with a through hole for receiving the breast to be examined; a mounting frame for mounting the supporting table and equipped with at least one actuator for adjusting the supporting table in height; the supporting table is divided into a first portion and second portion along an axis; the first portion is smaller in extension along the longitudinal axis than the second portion and is provided with the through hole; the two portions are movably connected to each other.

17 Claims, 5 Drawing Sheets

(56) References Cited

U.S. PATENT DOCUMENTS

| | | | |
|---|---|---|---|
| 6,883,194 B2* | 4/2005 | Corbeil | A61B 5/0091 378/37 |
| 2005/0172405 A1* | 8/2005 | Menkedick | A61B 5/1115 5/618 |
| 2009/0139029 A1* | 6/2009 | Rawls-Meehan | A61G 7/015 5/617 |
| 2012/0131749 A1* | 5/2012 | Taku | A61B 5/0091 5/600 |

* cited by examiner

DEVICE FOR SUPPORTING A PATIENT TO ALLOW PERFORMANCE OF A BREAST EXAM

This application claims priority to Italian Patent Application BO2014U000080 filed Sep. 30, 2014, the entirety of which is incorporated by reference herein.

BACKGROUND OF THE INVENTION

This invention relates to a device for supporting a patient to allow a breast exam to be performed.

At present, apparatuses are known which are used to perform a breast exam, in particular mammography and/or tomosynthesis, and which comprise a source configured to emit X-rays and a detector configured to receive the X-rays emitted by the source.

It should also be noted that these apparatuses may also be equipped with a stereotactic biopsy system.

This system is a method for computing the exact position of a region of interest in the breast by capturing images of it at predetermined angles relative to a fulcrum of rotation and of a probe (which may or may not be motor-driven) for extracting the cut tissue.

The two main approaches to stereotactic biopsy involve performing the biopsy in a reclining position or in a standing position.

Generally speaking, it is preferable to have the possibility of performing the biopsy with the patient reclining in the prone position (face down on a dedicated table above the detector) because in most cases this makes the patient more comfortable, reducing the risk of movements during the exam and making the breast more accessible.

It has also been shown that vasovagal reactions (fainting) are less frequent in the prone position.

At present, devices for supporting the patient which also allow the exam to be performed in the reclining position have a main supporting table extending horizontally along a longitudinal axis of extension.

If the support has to allow the exam to be performed with the patient reclining either in the prone or lateral decubitus position, the table also has a hole at one end, through which the patient's breast passes and is held in place.

The supporting table is mounted on top of a frame (provided with wheels to allow movement) and on one or more actuators for vertically adjusting the supporting table (usually telescopic columns) so as to position the patient most suitably according to the height of the probe and the position of the area of the breast to be examined.

A supporting device structured in this way, however, has some disadvantages.

More specifically, a horizontal supporting table having a structure of this kind may bend at the ends of it under the patient's weight, thus causing positioning problems when the probe approaches.

That means the tissue at the edge of the viewing field may not be displayed clearly when the supporting device and the image capturing system are not coupled closely enough (on account of possible collisions).

As a result, positioning operations take longer because they have to be repeated following a different approach (repositioning either the supporting device or the patient) and in some cases it may even be impossible to perform the exam at all. The completely horizontal supporting table also makes it difficult and awkward for the patient to climb onto the table and get into the right position before the exam and to get off the table when the exam is over.

Indeed, the patient has to move into a prone position and at the same time place the breast inside the opening and vice versa (that is, get up again) along a completely straight and horizontal surface.

These difficulties are even worse in the case of elderly people and people with weight or back problems.

Another problem, partly connected with the previous one, is the difficulty of positioning and adjusting the breast relative to the rest of the patient's body inside the access hole, which is usually made in a central position (relative to the width of the supporting table) and thus forces the patient to adopt an off-center position relative to the support, with the right shoulder protruding when the exam regards the left breast, and vice versa.

To date, there are no means of adjusting the distance between the hole and the end of the supporting device to adapt to the wide variety of head-to-thorax measurements in different patients: thus, tall patients might have no head support on the supporting device and be subjected to the discomfort of muscular strain to hold their heads up until the exam is over.

SUMMARY OF THE INVENTION

This invention has for an aim to provide a device for supporting a patient to allow a breast exam to be performed and which overcomes the above mentioned drawbacks of the prior art.

More specifically, the aim of this invention is to provide a device for supporting a patient while an exam is performed on the patient's breast, which makes it quick and easy for the patient to get into the right position and which makes it safe and fast to position the patient relative to the exam device or probe.

A further aim of the invention is to provide a device for supporting a patient while an exam is performed on the patient's breast, which allows the breast to be positioned on the device easily and comfortably, without requiring the patient to exert added effort and guaranteeing the comfort of the required position for the entire duration of the exam.

These aims are fully achieved by the device for supporting a patient during a breast exam forming the object of this utility model and as characterized in the appended claims.

More specifically, the supporting device allowing an exam to be performed on a patient's breast comprises a supporting table which has a longitudinal axis of extension and on which the patient can lie in a reclining position.

In proximity to one end of it, the supporting table is provided with a through hole for receiving the breast to be examined.

The device also comprises a mounting frame for the supporting table and at least a pair of actuators for adjusting the supporting table in height relative to a walkable reference floor.

According to this invention, the supporting table of the device is divided into a first and second portion, which are distinct from each other, along an axis transversal to the longitudinal axis of extension.

Also according to this invention, the first portion of the device is smaller in extension along the longitudinal axis than the second portion and is provided with the through hole.

Also according to this invention, the two portions of the device are movably connected to each other.

Also according to this invention, the device further comprises movement and adjustment means for the smaller first portion for moving the first portion from a neutral condition, where it is co-planar with the second portion, to two or more stable operating conditions where the first portion is inclined (rotated) relative to the second portion at predetermined angles, including angles opposite in sign, relative to the neutral condition.

Thanks to this structure, the device gives the possibility, before and after the exam, of adjusting the position of the upper part of the patient's body and of the breast to be examined.

In particular, the adjustable portion can, for example, be positioned downwards (negative angle of inclination) and then returned to a neutral or positive angle according to operating needs (size of breast and position of the part of the breast to be examined, type of exam to be performed, type and size of the apparatuses).

BRIEF DESCRIPTION OF THE DRAWINGS

These and other features of the invention will become more apparent from the following detailed description of a preferred, non-limiting embodiment of it, with reference to the accompanying drawings, in which.

DESCRIPTION OF THE PREFERRED EMBODIMENTS

Figure 1:
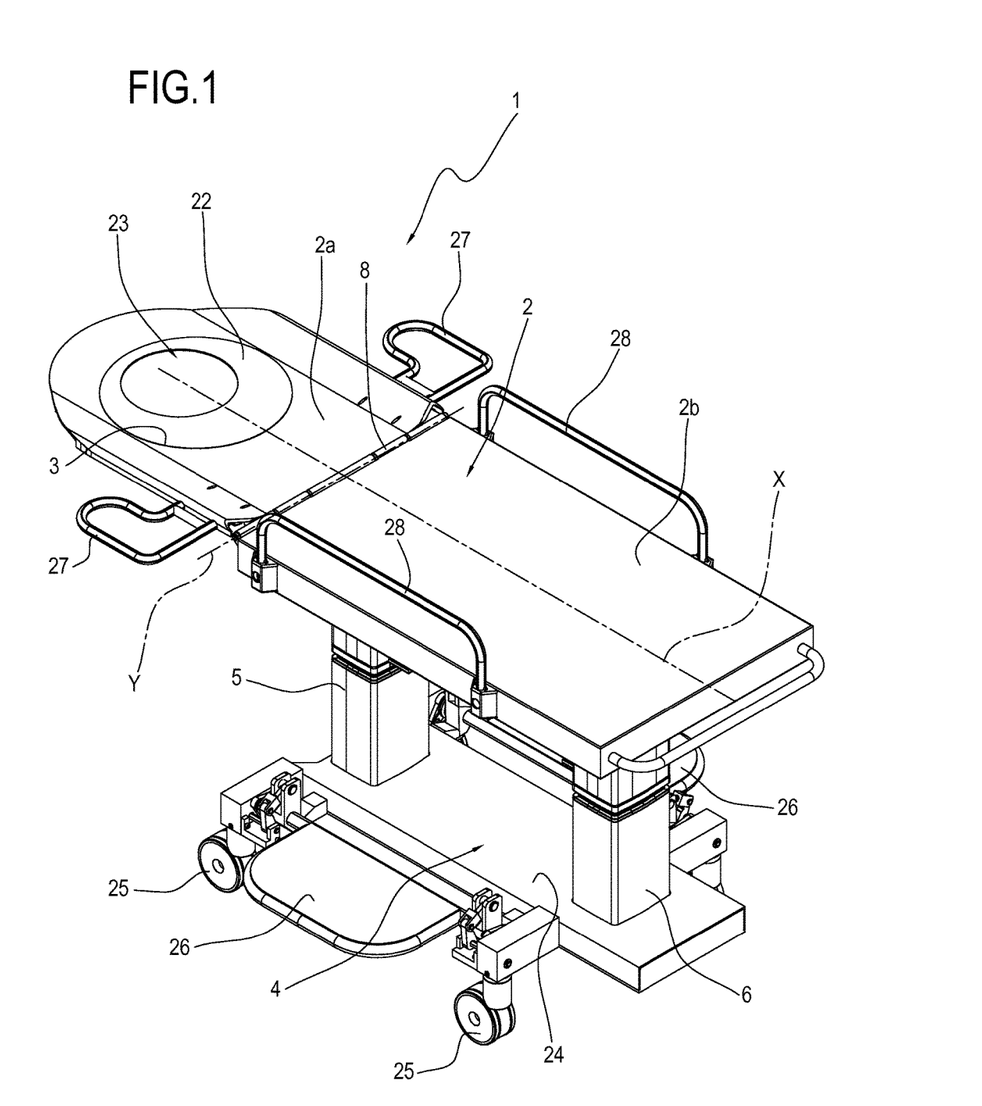
FIG. 1 is a top perspective view of a device according to this invention, for supporting a patient while an exam is performed on the patient's breast.
Figure 2:
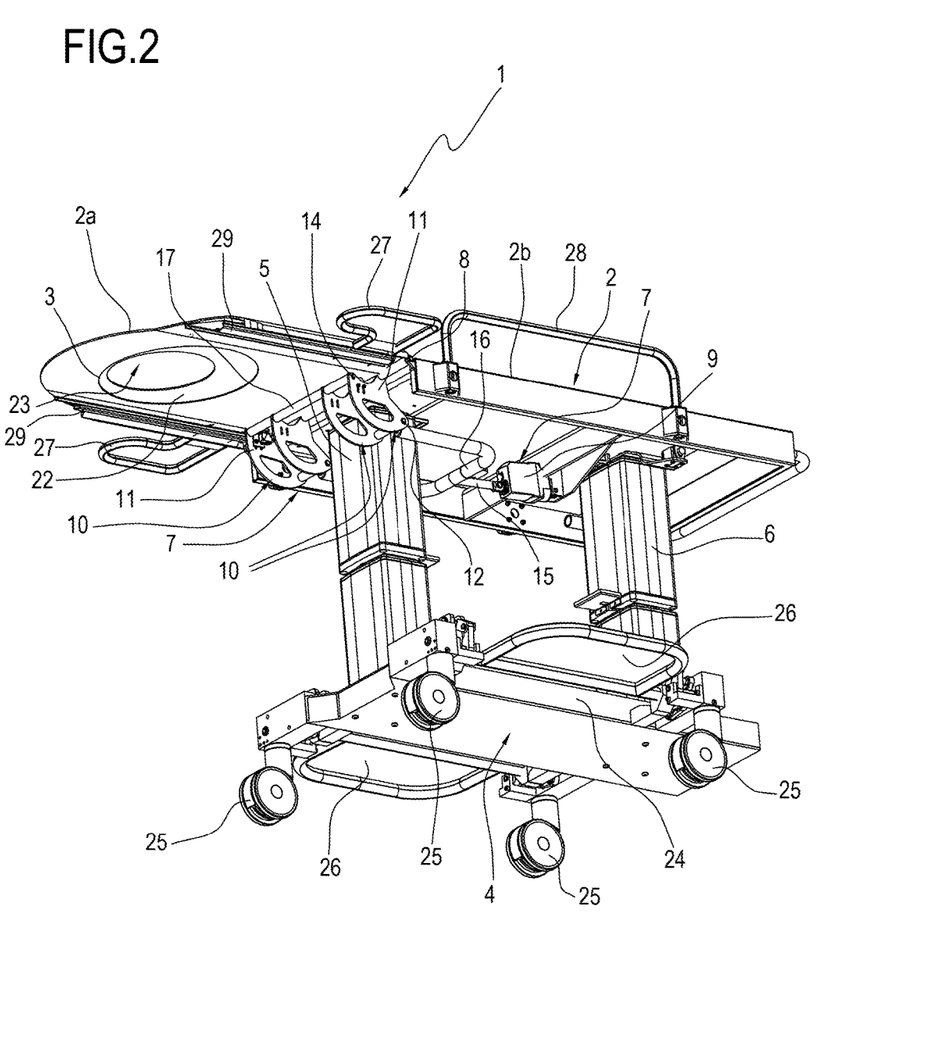
FIG. 2 shows the device of FIG. 1 in a perspective view from below.
Figure 3:
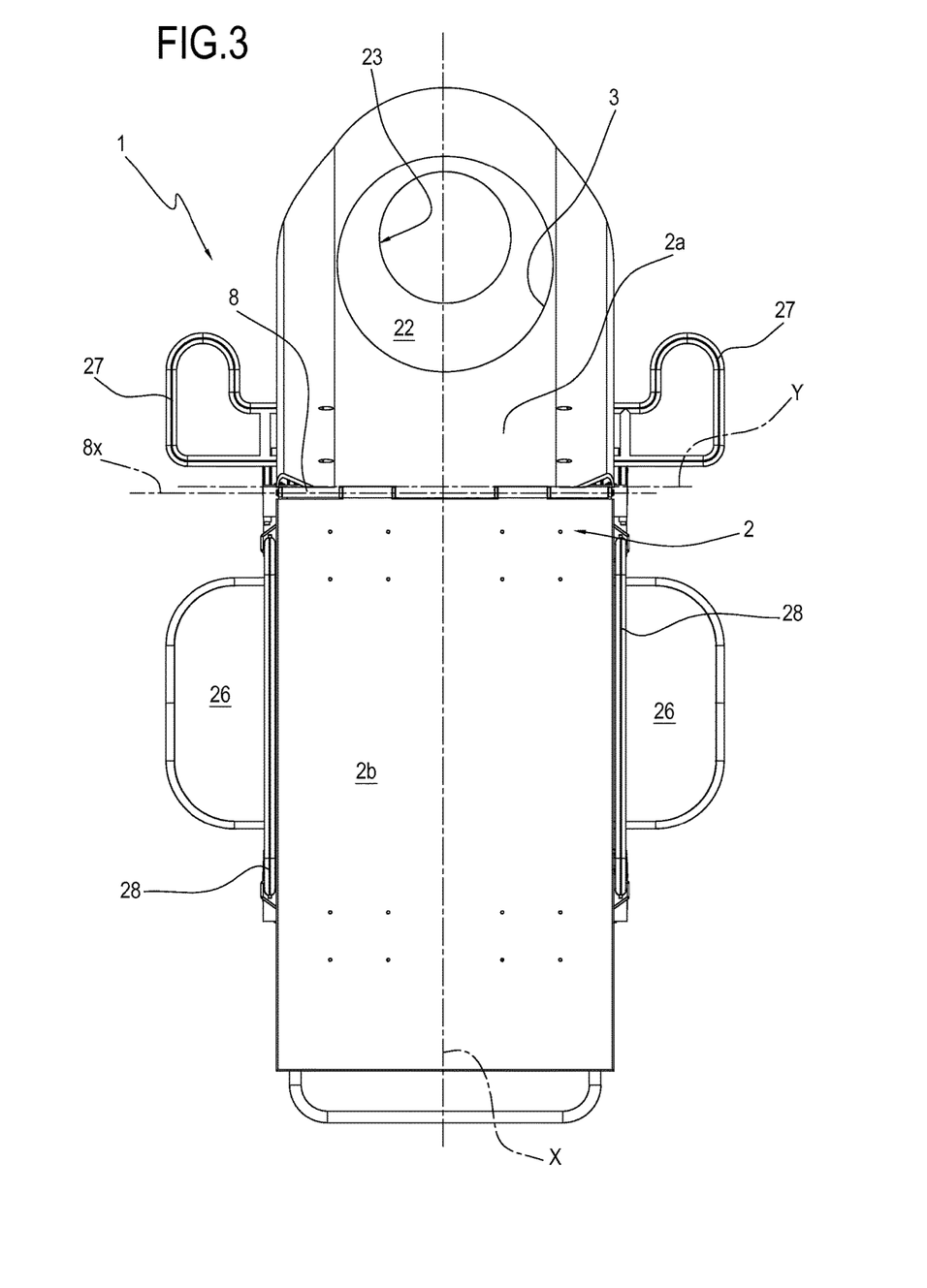
FIG. 3 shows the device of the preceding figures in a top plan view.
Figure 4:
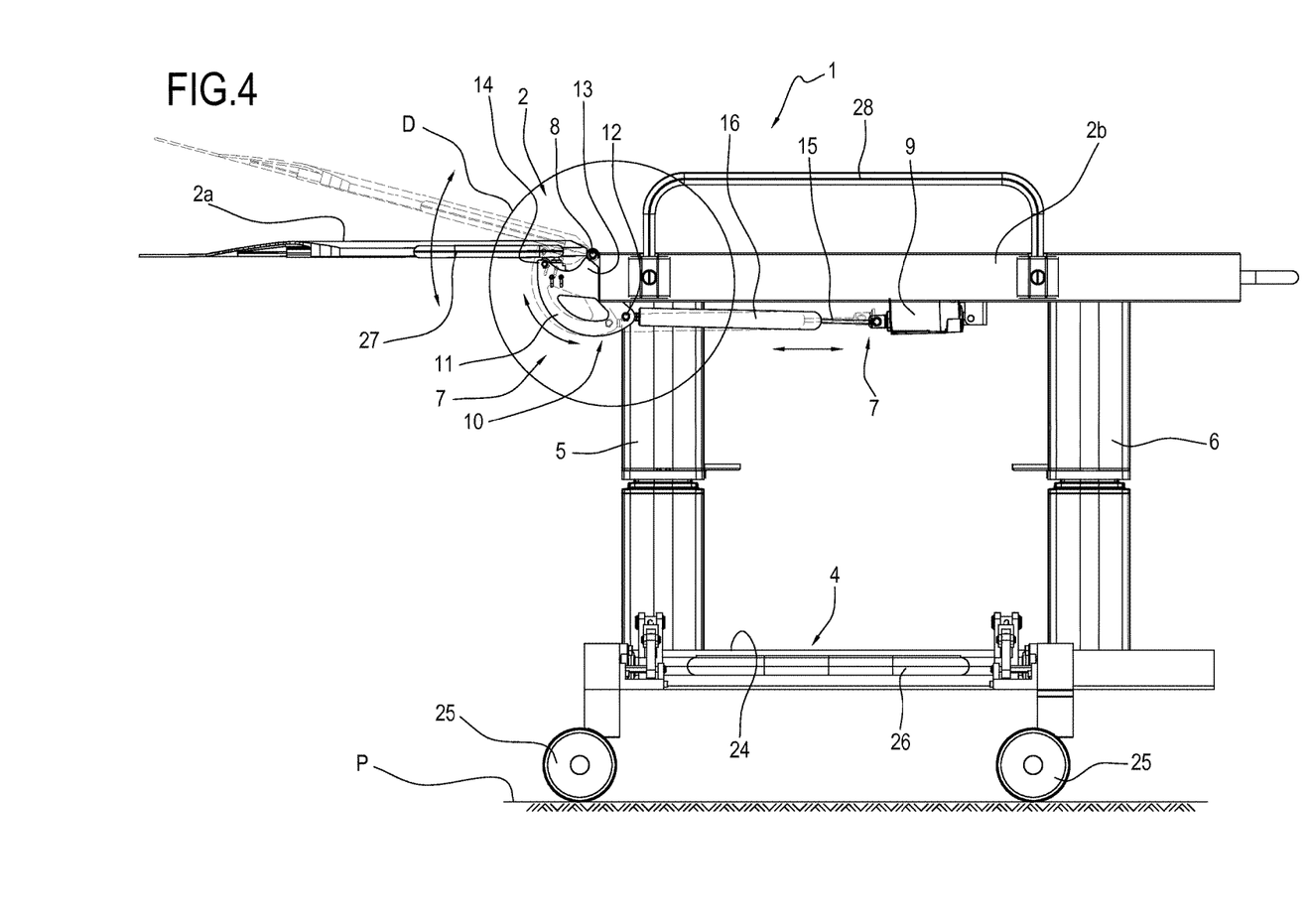
FIG. 4 shows the device of the preceding figures in a side view and with a portion of a supporting table in two different operating configurations.

With reference to the accompanying drawings and, in particular, FIGS. 1 to 3, the supporting device of this invention, denoted in its entirety by the numeral 1, is used to support patients undergoing a breast exam.

The device 1 comprises a supporting table 2 which has a longitudinal axis of extension X and on which the patient (not illustrated) can lie in a reclining position.

The supporting table 2 is provided, preferably in proximity to one end of it, with a through hole 3 for receiving the breast to be examined.

The device 1 also comprises a mounting frame 4 for the supporting table 2 and at least a pair of actuators 5, 6 for adjusting the supporting table 2 in height relative to a walkable reference floor P.

According to this invention, the supporting table 2 of the device 1 is divided into a first portion 2a and second portion 2b, distinct from each other, along an axis Y transversal to the longitudinal axis of extension X.

According to one aspect of this invention, the first portion 2a of the device is smaller in extension along the longitudinal axis X than the second portion 2b and is provided with the through hole 3.

According to another aspect of the invention, the two portions 2a and 2b of the device 1 are movably connected to each other.

According to yet another aspect of this invention, the device 1 comprises movement and adjustment means 7 for the smaller first portion 2a for moving the first portion 2a from a neutral condition, where it is co-planar with the second portion 2b, to a plurality of stable operating conditions where the first portion 2a is inclined (rotated) relative to the second portion 2b at a plurality of angles, including angles opposite in sign, relative to the neutral condition.

In other words, the supporting table 2 is divided into two parts (2a and 2b) where the first portion 2a provided with the hole 3 can be inclined (upwards or even downwards) not only to help the patient to settle and place her breast in the hole 3 but also to help operators position the patient in the prone position at the exam apparatus.

Preferably, the device 1 comprises a hinge element 8 for articulatedly connecting the first and second portions 2a and 2b to each other.

In light of this, the hinge element 8 is positioned with its axis 8X parallel to the transversal axis Y which separates the two portions 2a and 2b, and co-planar with the plane defined by the two portions 2a and 2b of the supporting table 2.

It should be noted that the hinge element 8 consists (by way of non-limiting example) of a cylindrical rod movably connecting the first portion 2a to the second portion 2b.

Preferably, the movement and adjustment means 7 are located under the supporting table 2 and are operatively in contact with the first portion 2a in such a way as to rotate the selfsame first portion 2a about the hinge element 8 (that is, about the axis 8X).

Also preferably, the movement and adjustment means 7 comprise an actuator 9 and a linkage 10 (see FIGS. 2, 4, 5 and 6).

In light of this, the linkage 10 is composed of at least one shaped operating element 11 having a pair of lobes 12 and 13 and defining corresponding points of articulation with the actuator 9 and, respectively, with the hinge element 8 about which the operating element 11 rotates.

It should be noted that the operating element 11 has a third lobe 14 which, in use, is positioned under the first portion 2a and in contact with the first portion 2a (with the underside surface thereof) in such a way as to define a guidance zone for moving the first portion 2a about the axis 8X of the hinge element 8.

In a preferred embodiment, the linkage 10 comprises at least a pair of operating elements 11, each positioned at one lateral edge of the first portion 2a.

In this embodiment, the actuator 9, which is a linear actuator, is associated with the underside of the second portion 2b of the supporting table 2.

In light of this, the actuator 9 is connected to a rigid arm 15 (that is, to the end of the arm 15).

The arm 15 in turn comprises a forked branch 16 (branching off from the free end of the arm 15) which is articulated, at the ends of it, to a corresponding vertex defined by the lobes 12 of the operating elements 11.

Thanks to this structure, the action of the actuator 9, in one direction or the other, applies a balanced pushing or pulling action on the operating elements 11, thus determining a precise and modulated movement of the first portion 2a of the table 2.

At a structural level (as shown in the drawings) four operating elements 11 are used to obtain optimum and precise movement and to steadily support the first portion 2a of the table 2 in height when it has to support the front portion of the patient.

Figure 5:
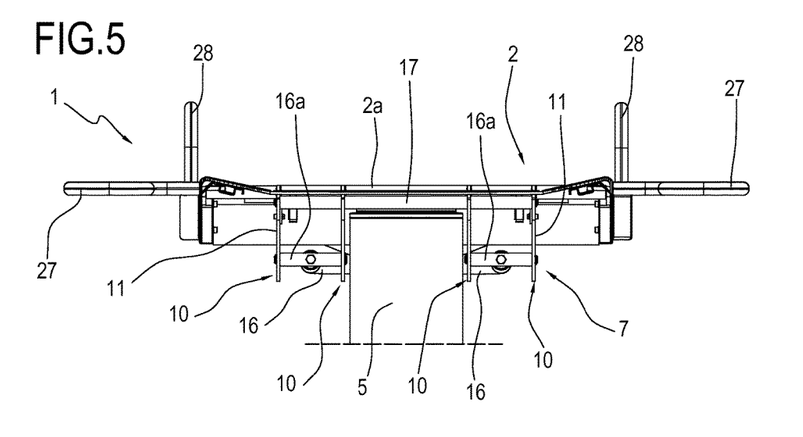
FIG. 5 illustrates the device of the preceding figures in a front face view, with some parts cut away in order to better illustrate others.
Figure 6:
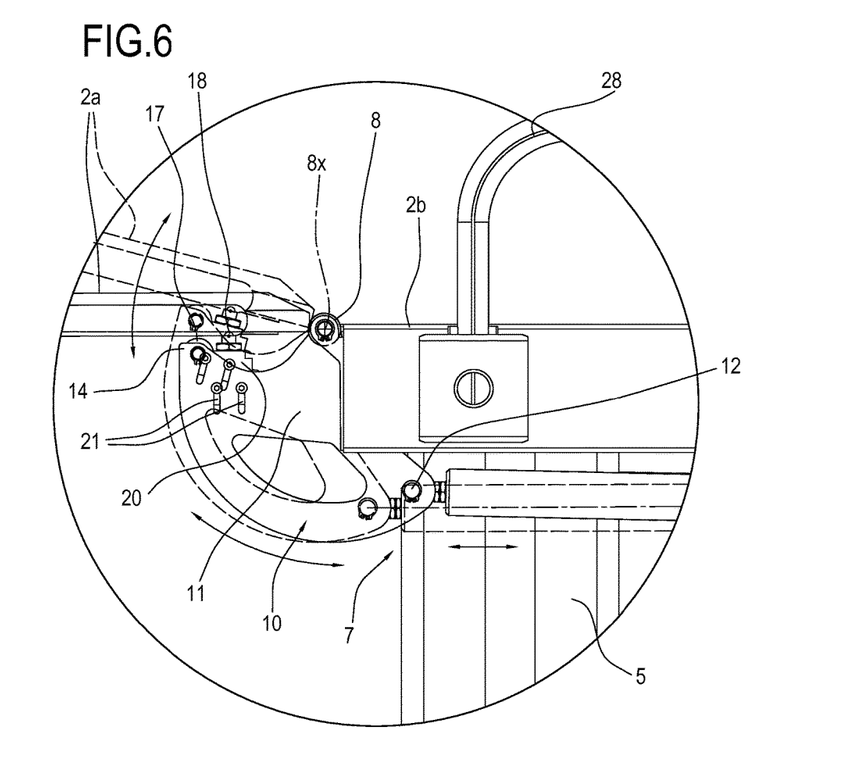
FIG. 6 shows a scaled up detail D from FIG. 4.

Indeed, as shown in FIG. 5, the four lobes 12 are connected (articulated) in pairs to the fork 16 by means of a corresponding transverse rod 16a in such a way as to coordinate all the operating elements 11 simultaneously when the actuator 9 is activated.

Further, the operating elements 11 are joined to each other by a supporting and stiffening shaft 17 (with circular cross section) which is rotatably connected at the corresponding third lobe 14 and whose axis of extension is parallel to the axis 8X of the hinge element 8.

Thanks to this shaft 17 (as will be seen later in this specification), the operating elements 11 define a supporting surface for the first portion 2a, particularly when there is a weight (the patient) bearing down on the first portion 2a, keeping the first portion 2a correctly in place.

To make each operating element 11 structurally stiffer, the operating element 11 itself has a rigid, arcuate fitting at the bottom of it which connects the lobe 12 (point of articulation with the actuator 9) to the lobe 14 (point of connection to the shaft 17).

Preferably, the supporting device 1 comprises at least one sensor 18, configured to detect contact between the inside of the first portion 2a and the linkage 10 (in particular the operating element 11).

Preferably, the sensor 18 is of the ON-OFF type.

More preferably, the sensor 18 is a switch.

Still more preferably, the sensor 18 is a microswitch.

The sensor 18 is preferably fixed to the first portion 2a, or alternatively, to the linkage 10.

The sensor 18 is preferably connected to at least one of the actuators (5,6,9) to disable it if no contact between the inside of the first portion 2a and the linkage 10 is detected.

This corresponds to an anomalous operating condition.

Thus, the movements of the supporting device 1 are advantageously interrupted if contact between the operating element 11 and the underside of the first portion 2a is lost (as might happen, for example, if the portion 2a, during the downward movement of the supporting table 2 or during the movement of the portion 2a only, collides with something that prevents it from moving further).

It should be noted that the first portion 2a protrudes in cantilever fashion from the second portion 2b so as to be able to move/rotate freely without any other mechanical constraints.

In light of this, the second portion 2b of the supporting table 2 is associated with, and mounted on, the aforementioned frame 4 and the aforementioned pair of height adjustment actuators 5 and 6.

It should be noted that the frame 4 comprises a lower base 24 to which wheels 25 for moving the supporting device 1 are rotatably connected.

Articulated to each side of the lower base 24 there are footboards 26 to help the patient climb onto the supporting table 2.

The footboards 26 also operate on the wheels of the supporting device 1 to lock/unlock them as required.

More specifically, moving the footboards 26 to the lowered position locks the wheels and allows the patient to climb onto the supporting table 2 safely (with the device 1 securely stopped).

When the footboards 26 are moved to the raised position, on the other hand, the wheels are unlocked (and thus free to turn) to enable the supporting device 1 to be moved about.

Advantageously, the fact that the footboards 26 are raised when the supporting device 1 is moved about reduces the risk of the footboards 26 colliding with other objects during movement.

The fixed part of each actuator 5 and 6 is mounted on the lower base 24, while the movable, telescopic part of each actuator 5 and 6 is associated with the second portion 2b.

The second portion 2b is also provided with a pair of safety rails 28 to laterally contain the patient's body and thus prevent the patient from falling off the supporting table 2.

The first portion 2a is also provided with armrests 27 to support the patient's arms when the patient has to adopt a position with arms extended away from the bust.

The armrests 27 are preferably extractable.

The device 1 also comprises a disk 22 for partially filling the hole 3 of the first portion 2a and which is engaged in the hole 3 itself (FIGS. 1 and 3).

The disk 22 has an opening 23 which is smaller in diameter than the hole 3 and which is eccentric relative to the center of the hole 3.

The opening 23 is the one which, in use, actually receives the patient's breast.

It should be noted that the disk 22 is movably coupled to the edges defining the hole 3 in such a way that it can rotate about the center of the hole 3 to allow adjusting the position of the eccentric opening 23 on the first portion 2a.

In short, the eccentric opening 23 combined with the possibility of rotating the cover disk 22 allows positioning the zone of entry of the breast to be examined in such a way that it coincides with the zone on the right or left of the axis of longitudinal extension of the first portion 2a, thus facilitating operations also for the patient.

In other words, thanks to the cover disk 22, the position of the eccentric opening 23 relative to the first portion 2a can be adjusted.

Advantageously, the edge of the disk 22 is engaged in a circular groove (not illustrated) of the hole 3, allowing it to rotate around the hole itself.

A supporting device structured in this way thus achieves the preset aims thanks to the presence of a portion which is angularly adjustable relative to the rest of the supporting table.

This device guarantees:

that the patient can be positioned more easily on the supporting table;

that the position of the breast can be adapted more quickly relative to the exam apparatus, with the patient already in position (correction of deformation caused by the patient's weight);

that it is easier for the patient to climb down, thanks to the possibility of modifying the angle of the front supporting zone;

that patients with back problems have less difficulties during exam operations.

Also, the presence of the adjustable disk with the eccentric hole facilitates operations to position the breast correctly with the patient in a comfortable position on the supporting table and avoiding the discomfort of awkward positions.

It should also be noted that the presence of the adjustable disk 22 and, more in general, the possibility of adjusting the position of the opening 23 defined by the hole itself means that the supporting device 1 always offers the minimum distance between the hole and the end of the support, thus reducing the risk of collisions.

Indeed, according to the invention, for the patient to rest correctly on the device it is not necessary to design the distance between the hole and the end of the support according to maximum patient height. This would have been the only possibility permitted in the prior art but such a design choice would have excessively increased the cases of the exam failing on account of collisions between the patient support and exam apparatus. Thus, in order to increase the probability of the exam succeeding, the preferred approach was to disregard the patient's comfort in all exams.

The possibility of adjusting the position of the opening 23 means that the patient's comfort is the rule and not the exception.

According to another aspect, not illustrated, the device 1 comprises at least one light source 29, located under the first portion 2a. See FIG. 2.

Thus, the exam area (the region under the hole 3) is optimally illuminated by means of one or more light sources 29.

In a first embodiment, the at least one light source 29 is fixed to the first portion 2a.

In another embodiment, the at least one light source 29 is fixed to the operating element 11.

In yet another embodiment, the device 1 comprises a plurality of light sources 29, located under the first portion 2a, a first plurality of the light sources 29 being fixed to the first portion 2a and a second plurality of the light sources 29 being fixed to the operating element 11.

Preferably, the light source 29 comprises one or more LEDs.

Preferably, the light source 29 consists of a bar equipped with LEDs.

Still more preferably, the device 1 is equipped with three LED bars arranged in a U shape.

Preferably, one of the three LED bars is fixed to the operating element 11 and the other two are fixed to the underside of the first portion 2a.

What is claimed is:

1. A device for supporting a patient to allow an exam to be performed on the patient's breast, comprising:
   a supporting table which has a longitudinal axis of extension and on which the patient can lie in a reclining position; the supporting table including, in proximity to one end of the supporting table, a through hole for receiving the breast to be examined;
   a mounting frame mounting the supporting table and including at least one height adjustment actuator for adjusting the supporting table in height relative to a walkable reference floor, wherein the supporting table is divided into a first portion and a second portion, distinct from each other, along an axis transversal to the longitudinal axis of extension; the first portion being smaller in extension along the longitudinal axis than the second portion and including the through hole; the first and second portions being movably connected to each other;
   a movement and adjustment device for adjusting an inclination of the first portion and configured to move the first portion from a neutral condition, where the first portion is co-planar with the second portion, to a plurality of stable operating conditions where the first portion is inclined relative to the second portion at a plurality of angles and declined relative to the second portion at a plurality of angles, relative to the neutral condition;
   wherein the second portion is associated with, and mounted on, the mounting frame and the at least one height adjustment actuator;
   a disk rotatably engaging the through hole and partially filling the through hole; the disk including an opening which is smaller in diameter than the through hole and which is positioned eccentric on the disk relative to a center of the through hole; the disk being rotatable around a center of the through hole to allow adjusting a position of the opening with respect to the through hole, wherein the opening passes through the disk and is completely surrounded by the disk.

2. The device according to claim 1, wherein the at least one height adjustment actuators includes at least a pair of height adjustment actuators for adjusting the supporting table in height relative to the walkable reference floor.

3. The device according to claim 1, comprising a hinge for articulatingly connecting the first portion and the second portion to each other; the hinge having an axis and being positioned with the axis parallel to the transversal axis which separates the two portions, and co-planar with a plane defined by the first and second portions.

4. The device according to claim 3, wherein the movement and adjustment device comprises an inclination actuator and a linkage; the linkage including a shaped operating element having a pair of lobes and defining corresponding points of articulation with the inclination actuator and, respectively, with the hinge about which the operating element rotates; a third lobe of the shaped operating element being, in use, positioned under the first portion and in contact with the first portion to define a guidance zone for moving the first portion about the axis of the hinge.

5. The device according to claim 4, wherein the linkage comprises a pair of operating elements, each positioned at one lateral edge of the first portion, and wherein the inclination actuator is a linear actuator and is associated with an underside of the second portion; the linkage including a rigid arm comprising a forked branch which is articulated, at ends of the forked branch, to a corresponding vertex defined by lobes of the operating elements; the inclination actuator being connected to the rigid arm.

6. The device according to claim 5, and further comprising a supporting and stiffening shaft, and wherein the operating elements are joined to each other by the supporting and stiffening shaft which is rotatably connected at the corresponding third lobe and whose axis of extension is parallel to the axis of the hinge.

7. The device according to claim 4, and further comprising a sensor configured to detect contact between an inside of the first portion and the linkage.

8. The device according to claim 7, wherein the sensor is operatively connected to at least one chosen from the at least one height adjustment actuator and the inclination actuator, to disable the device no contact between the inside of the first portion and the linkage is detected.

9. The device according to claim 4, and further comprising at least one light source positioned under the first portion.

10. The device according to claim 1, wherein the movement and adjustment device is positioned under the supporting table and is operatively in contact with the first portion to rotate the first portion about a hinge element by which the first portion and the second portion are articulated to each other.

11. The device according to claim 1, and further comprising a light source positioned under the first portion.

12. The device according to claim 11, wherein the light source is fixed to the first portion.

13. The device according to claim 1, wherein the movement and adjustment device comprises an inclination actuator and a linkage; the linkage including a shaped operating element having a pair of lobes and defining corresponding points of articulation with the inclination actuator and, respectively, with a hinge about which the operating element rotates; a third lobe of the shaped operating element being, in use, positioned under the first portion and in contact with the first portion to define a guidance zone for moving the first portion about the axis of the hinge, and further comprising a plurality of light sources, located under the first portion, a first plurality of the light sources being fixed to the first portion.

14. The device according to claim 1, wherein the mounting frame comprises a lower base; and further comprising:
a plurality of wheels for moving the device mounted to the lower base;
a footboard articulated to the lower base to provide a step for a patient climbing on to the supporting table;
wherein the footboard operates on at least one of the plurality of wheels to lock the at least one of the plurality of wheels and securely stop the device when stepped on by the patient and to unlock the at least one of the plurality of wheels to allow movement of the device when stepped off by the patient.

15. The device according to claim 14, wherein the footboard is movable between a lowered position to provide the step and a raised position to reduce a risk of collision of the floorboard with other objects during movement of the device.

16. The device according to claim 1, wherein the mounting frame comprises a lower base; and further comprising:
a plurality of wheels for moving the device mounted to the lower base;
a footboard articulated to the lower base;
wherein the footboard is movable between a lowered position to provide a stepping position for enabling a patient to climb onto the device and a raised position to reduce a risk of collision of the floorboard with other objects during movement of the device.

17. The device according to claim 1, wherein the disk engages a circular groove of the supporting table bordering the through hole.

* * * * *